US 8,398,746 B2

(12) United States Patent
Black et al.

(10) Patent No.: US 8,398,746 B2
(45) Date of Patent: Mar. 19, 2013

(54) SMALL AREA ELECTROSTATIC AEROSOL COLLECTOR

(75) Inventors: Rodney S. Black, Galloway, OH (US); Edgar Fogelman, Charlottesville, VA (US); Kevin T. Hommema, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 0 days.

(21) Appl. No.: 13/212,437

(22) Filed: Aug. 18, 2011

(65) Prior Publication Data

US 2011/0315011 A1 Dec. 29, 2011

Related U.S. Application Data

(63) Continuation of application No. PCT/US2010/024389, filed on Feb. 17, 2010.

(60) Provisional application No. 61/153,335, filed on Feb. 18, 2009.

(51) Int. Cl.
*B03C 3/36* (2006.01)
(52) U.S. Cl. ............... 95/78; 95/79; 96/63; 96/77; 96/96
(58) Field of Classification Search ............... 95/78, 79; 96/60, 62, 63, 77, 96, 97; 118/715, 719, 118/722
See application file for complete search history.

(56) References Cited

U.S. PATENT DOCUMENTS

| 3,295,440 | A | * | 1/1967 | Rarey et al. | 101/114 |
|---|---|---|---|---|---|
| 3,526,828 | A | | 9/1970 | Whitby | |
| 3,585,060 | A | * | 6/1971 | Gourdine et al. | 427/460 |
| 4,284,496 | A | | 8/1981 | Newton | |
| 4,531,486 | A | | 7/1985 | Reif et al. | |
| 5,098,657 | A | | 3/1992 | Blackford et al. | |
| 5,647,890 | A | * | 7/1997 | Yamamoto | 95/69 |
| 6,206,970 | B1 | * | 3/2001 | Atwell | 118/715 |
| 7,381,246 | B1 | * | 6/2008 | Zhao et al. | 96/60 |
| 7,550,035 | B1 | * | 6/2009 | Heckel et al. | 96/57 |
| 7,833,324 | B2 | * | 11/2010 | Chen et al. | 96/45 |

(Continued)

FOREIGN PATENT DOCUMENTS

| GB | 1105604 A | 3/1968 |
|---|---|---|
| GB | 2371362 A | 7/2002 |

(Continued)

OTHER PUBLICATIONS

Notification of Transmittal of the International Search Report and the Written Opinion of the International Searching Authority for PCT Application No. PCT/US2010/024389, Mailing Date of May 27, 2010; European Patent Office; Rijswijk, The Netherlands.

(Continued)

*Primary Examiner* — Richard L Chiesa
(74) *Attorney, Agent, or Firm* — Thomas E. Lees, LLC

(57) ABSTRACT

A small area electrostatic aerosol collector includes a collector housing, an inlet nozzle that extends from the housing and an exit port that provides an exit for air to flow back out of the housing. A pumping arrangement pulls air into the housing through the inlet nozzle. The sampled air is moved through ductwork such that particulates are collected on a substrate and the air is evacuated through the exit port after collection. The collector includes a charging device positioned within the ductwork to create an electric field defining a charging point that the air passes through between the inlet nozzle and the substrate. The substrate is held at a neutral or opposite charge relative to the electric field created by the charging device. Particulates are collected on the sample substrate by containing the aerosol in a small area and by forcing the aerosol to flow near the substrate.

20 Claims, 5 Drawing Sheets

U.S. PATENT DOCUMENTS

| | | | |
|---|---|---|---|
| 2003/0200787 A1 | 10/2003 | Totoki | |
| 2005/0068040 A1 | 3/2005 | Mitchell et al. | |
| 2005/0126260 A1 | 6/2005 | Totoki | |
| 2007/0234901 A1* | 10/2007 | Pletcher et al. | 95/78 |
| 2008/0250926 A1* | 10/2008 | Riskin | 95/57 |
| 2010/0132561 A1* | 6/2010 | Bromberg et al. | 96/54 |

FOREIGN PATENT DOCUMENTS

| | | |
|---|---|---|
| JP | 53-130582 A * | 11/1978 |
| JP | 61046443 U | 3/1986 |
| WO | 2008/130135 A1 | 10/2008 |
| WO | 2009/108795 A1 | 9/2009 |

OTHER PUBLICATIONS

Japanese Office Action dated Sep. 25, 2012 for Japanese Patent Application No. 2011-551175, Battelle Memorial Institute, which is based on PCT/US2010/024389, filed on Feb. 17, 2010. The present U.S. application is also based on the same PCT application.

Partial English Translation of Japanese Office Action dated Sep. 25, 2012 for Japanese Patent Application No. 2011-551175, Battelle Memorial Institute, which is based on PCT/US2010/024389, filed on Feb. 17, 2010. The present U.S. application is also based on the same PCT application.

Partial translation of Japanese reference JP 61046443U, cited in Japanese Office Action dated Sep. 25, 2012 for Japanese Patent Application No. 2011-551175, Battelle Memorial Institute, which is based on PCT/US2010/024389, filed on Feb. 17, 2010. The present U.S. application is also based on the same PCT application.

* cited by examiner

SMALL AREA ELECTROSTATIC AEROSOL COLLECTOR

CROSS REFERENCE TO RELATED APPLICATIONS

This application is a continuation of International Application No. PCT/US2010/024389, filed Feb. 17, 2010, entitled "SMALL AREA ELECTROSTATIC AEROSOL COLLECTOR", which claims the benefit of U.S. Provisional Patent Application Ser. No. 61/153,335, filed Feb. 18, 2009, entitled "SMALL AREA ELECTROSTATIC AEROSOL COLLECTOR", the disclosures of which are hereby incorporated by reference.

BACKGROUND

The present invention relates in general to bioaerosol collection, and in particular, to a small area electrostatic aerosol collector.

The monitoring of airborne bioaerosols has received an increasing amount of attention in recent years because of the potential impact of particulates on radiative and climatic processes, on human health and because of the role particles play in atmospheric transport and deposition of pollutants. For example, it may be desirable to analyze the air in a predetermined location for particulates that fall within a range of sizes that can be inhaled, such as naturally occurring or artificially produced airborne pathogens, allergens, bacteria, viruses, fungi and biological or chemical agents that are found in or are otherwise introduced into the location.

As another example, it may be desirable to detect the presence of predetermined types of airborne particulates in semiconductor clean rooms, pharmaceutical production facilities and biotechnology laboratories to verify that there has been no contamination produced in such environments that would create undesirable environmental exposures or adversely affect manufacturing, testing or experimental processes. Similarly, the ability to detect the presence of particular airborne particulates in hospitals, nursing homes, rehabilitation centers and other care facilities may be beneficial to assist in preventing the spread of disease, infection or harmful bacteria.

The monitoring of atmospheric particulate matter further finds applications for the assessment of human health risk and for the assessment of environmental contamination. Still further, the monitoring of atmospheric particulate matter further finds applications for the assessment of compliance with National Air Quality Standards (NAAQS), e.g., to monitor the air in public and commercial building air purification and distribution systems, work sites such as mines, sewage facilities, agricultural and manufacturing facilities, outside areas such as street corners, flues, and smokestacks. Monitoring of atmospheric particulate matter also finds applications for monitoring locations where it is desirable to monitor environmental hygiene, such as residences exposed to microorganisms, plants or animals.

BRIEF SUMMARY

According to various aspects of the present invention, a small area electrostatic aerosol collector comprises a collector housing and a sample substrate receiving area within the collector housing. The small area electrostatic aerosol collector further comprises an inlet nozzle that extends from the collector housing to provide an inlet for air to flow from outside of the collector housing to the inside of the collector housing and a passageway for air to flow from the inlet nozzle to the sample substrate receiving area. The small area electrostatic aerosol collector still further comprises a charging device having an electrode that extends into the passageway at an angle non-parallel to the passageway such that the tip of the electrode is generally centered in the passageway and a high voltage power source coupled to the charging device.

A sample substrate having a collection surface is positioned in the sample substrate receiving area and a sampling operation is performed. The sampling operation is performed such that a pumping arrangement pulls air into the collector housing through the inlet nozzle, draws the air towards the sample substrate receiving area through the passageway, and evacuates air drawn into the collector housing. The high voltage power source causes the electrode of the charging device to create an electric field that charges particles in the air flowing past the electrode. Additionally, the collection surface of the sample substrate is held at one of: a neutral charge and an opposite charge, relative to the electric field created by the charging device. Under this arrangement, particulates are collected on the collection surface of the sample substrate by containing the aerosol in a small area within the passageway and by forcing the air to flow near the collection surface of the sample substrate such that the charged particles are attracted to the collection surface.

According to further aspects of the present invention, a method of collecting particulates comprises providing a collector housing and providing a sample substrate receiving area within the collector housing. The method further comprises providing an inlet nozzle that extends from the collector housing to provide an inlet for air to flow from outside of the collector housing to the inside of the collector housing and providing a charging device having an electrode that extends within the passageway.

The method further comprises performing a sampling operation. A sample substrate having a collection surface is positioned in the sample substrate receiving area. The sampling operation is thus performed by pulling air into the collector housing through the inlet nozzle so as to draw the air towards the sample substrate receiving area through a passageway, and by evacuating air drawn into the collector housing. The sampling operation is further performed by causing the electrode of the charging device to create an electric field that charges particles in the air flowing past the electrode, wherein the charging device creates the electric field for a short sampling time and then allows the electrode to dissipate sufficiently to reduce contamination buildup in the passageway. The sampling operation also comprises holding the collection surface of the sample substrate at one of: a neutral charge and an opposite charge, relative to the electric field created by the charging device.

The sampling operation further comprises collecting particulates on the collection surface of the sample substrate by containing the aerosol in a small area within the passageway and by forcing the air to flow near the collection surface of the sample substrate such that the charged particles are attracted to the collection surface.

BRIEF DESCRIPTION OF THE SEVERAL VIEWS OF THE DRAWINGS

The following detailed description of various aspects of the present invention can be best understood when read in conjunction with the following drawings, where like structure is indicated with like reference numerals, and in which.

DETAILED DESCRIPTION

Many current technologies for monitoring and analysis of impurities require that a sample is first collected and concentrated onto a sample substrate. According to various aspects of the present invention, a small area electrostatic collector is provided, which can be used to remove particulates including bioaerosol particles from the air and deposit them into a small area on a solid substrate at a high efficiency. Particles are charged prior to being deposited on the substrate using electrostatic forces caused by an electric field generated within the collector. The collector may be implemented in a small scale and may be configured to utilize small amounts of power as will be described in greater detail herein.

Figure 1:
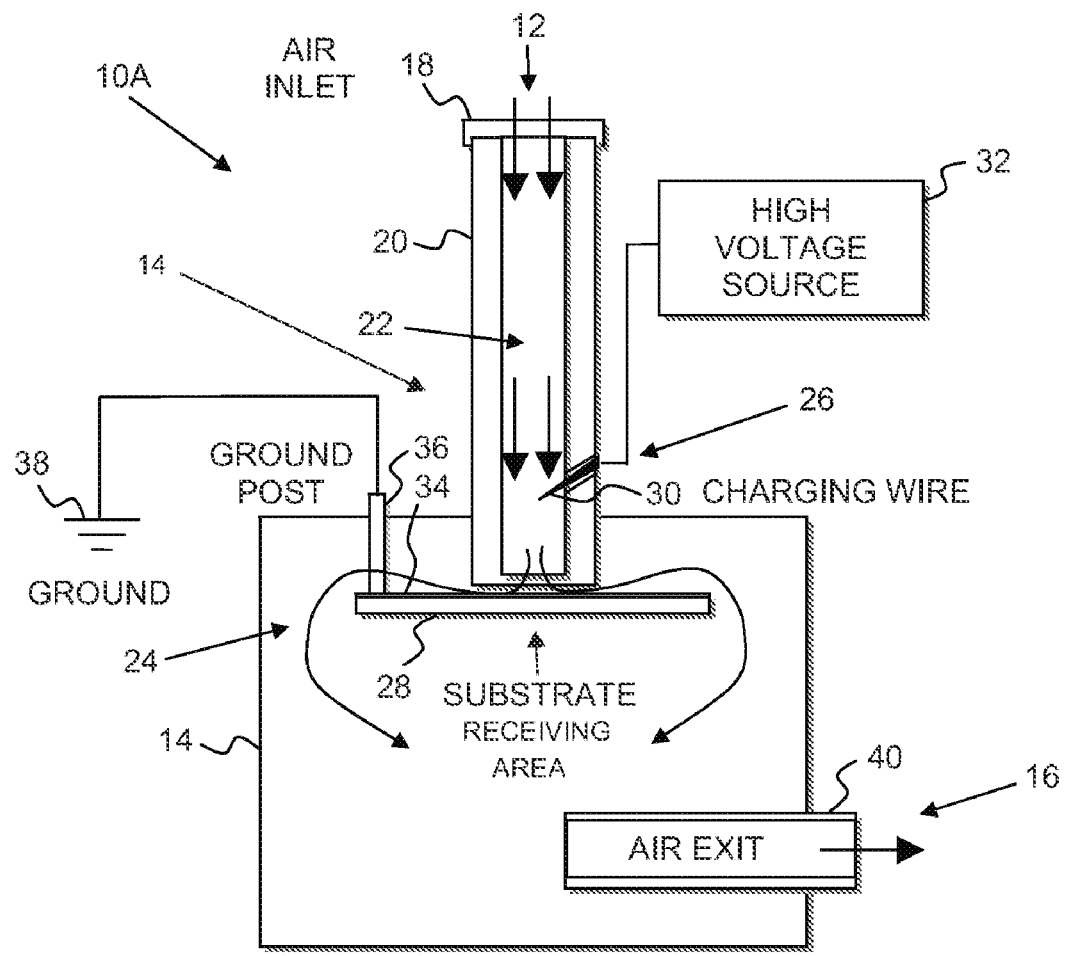
FIG. 1 is a schematic illustration of a small area electrostatic aerosol collector according to various aspects of the present invention.

Referring now to the drawings and in particular to FIG. 1, a small area electrostatic aerosol collector 10A is illustrated according to various aspects of the present invention. In general, air enters an aerosol entry port 12 of a housing 14 of the collector 10A. The sampled air is moved through ductwork such that particulates are separated from the air, and the air, stripped of the collected particles is exhausted from the housing 14 through an exit port 16. The aerosol may be any source of gas laden with particulates to be removed from the aerosol. A typical application, however, may comprise sampling ambient air.

To facilitate the entry of air, the aerosol entry port 12 of the collector 10A includes an inlet nozzle 18 that extends from the collector housing 14, e.g., via an inlet tube 20 of the collector housing 14, so as to provide an inlet for air to flow from outside of the collector housing 14 to the inside of the housing 14. The air enters the inlet nozzle 18 and passes through ductwork that directs the air flow within the housing 14. For example, as illustrated, the ductwork may include an inlet passageway 22 that passes through the inlet tube 20.

The air travels from the inlet passageway 22 to a collection section 24 before being exhausted from the housing 14 via the exit port 16. The collection section 24 includes in general, a charging device 26 and a sample substrate receiving area within the collector housing 14 for receiving a sample substrate 28 that collects particulates stripped from air that has traveled into the housing 14 through the inlet passageway 22. In an illustrative implementation, the inlet tube 20 is nonconductive, e.g., constructed of a polyacetal, such as Delrin® acetal resin by E. I. duPont and Co. of Wilmington Del.

The charging device 26 includes a portion thereof, which is positioned so as to create an electric field defining a charging point that the air passes through between the inlet nozzle 18 and the sample substrate 28. In the illustrative implementation of FIG. 1, the charging device 26 comprises an electrode, such as at least one charging wire 30, which extends within the passageway 22 that the air passes through within the housing 14. For example, the electrode may pass through the inlet tube 20 at an angle such that the tip of the electrode extends generally in the center of the inlet passageway 22 defining the ductwork. Moreover, the electrode may be adjustable within the passageway 22. This approach facilitates assembly and positioning of the electrode for desired operation. Moreover, the charging device 26 is electrically coupled to a high voltage power source 32. In this regard, the high voltage power source 32 generates several thousand volts of direct current (dc) power that is delivered to the electrode to create the electric field, as will be described in greater detail below.

The charging wire 30 may comprise a tungsten electrode or other suitable conductive material that is electrically connected to the high voltage power source 32. Moreover, the charging wire 30 preferably terminates in a point or generally pointed end. As such, the charging wire 30 may also be referred to herein as a charging needle, to characterize the electrode as being generally "needle shaped" according to various aspects of the present invention. In general, a dull tip on the electrode may result in less efficient operation, whereas a relatively sharper tip may be more efficient. However, the specific application will dictate the requirements of the electrode geometry.

The sample substrate 28 may comprise, for example, a slide such as an aluminum coated glass slide. In this regard, the slide may be secured within the sample substrate receiving area of the housing, e.g., using a spring biased retainer that secures the slide under the inlet tube 20 such that the slide can be easily replaced and/or changed. According to various aspects of the present invention, a collection surface 34 of the sample substrate 28 is in close proximity to the end of inlet tube 20, e.g., so close that an inspector may not be able to physically see the gap. As such, care may be required when changing slides to maintain proper calibration of the slide and end of the inner tube. As another example, the sample substrate may comprise an aluminum Mylar tape, e.g., for integration into automated sampling systems, e.g., by using a suitable roller and tensioner for winding and unwinding the Mylar tape.

Regardless of whether the sample substrate 28 is manually loaded or automatically fed into the housing 14, the collection surface 34 of the sample substrate 28 is held at a neutral or opposite charge relative to the electric field created by the electrode of the charging device 26. In an exemplary implementation, a grounding post 36 is electrically coupled to the sample collection surface 34 of the sample substrate 28. The grounding post 36 is tied to ground 38 and thus enables the sample collection surface 34 of the sample substrate 28 to be grounded relative to the electric field generated by the charging wire 30. In this regard, physical contact may be provided between the grounding post 36 and the sample collection surface 34 of the sample substrate 28.

A pumping arrangement 40 pulls air into the collector housing 14 through the inlet nozzle 18, draws the air towards the sample substrate receiving area 24 through the inlet passageway 22 and evacuates air drawn into the collector housing 14. As illustrated in FIG. 1, a single pump is utilized to implement the pumping arrangement 40, however, other arrangements may alternatively be implemented. The air (aerosol) is drawn by the pump 40 through ductwork, e.g., down the inlet tube 20 through the inlet passageway 22, and particulates are collected on the solid sample collection surface 34 of the sample substrate 28. The pump 40 further evacuates the air drawn into the collector housing 14 through the exit port 16. In this regard, the sample substrate 28 is positioned in close proximity to the end of the inlet tube. Moreover, the main pressure change occurs at the gap between the tube and substrate, which may be barely big enough for the air to pass through, as noted in greater detail herein. In an illustrative example, the pump pulls between approximately 1-3 liters of air per minute.

During operation of the collector 10A, a sample substrate 28 having a collection surface 34 is positioned in the sample substrate receiving area 24. The high voltage power source 32 causes the electrode of the charging device 26 to create an electric field that charges particles in the air flowing past the electrode. Further, the collection surface 34 of the sample substrate 28 is held at one of a neutral charge and an opposite charge, relative to the electric field created by the charging device 26. In this regard, particulates are collected on the collection surface 34 of the sample substrate 28 by containing the aerosol in a small area within the passageway 22 and by forcing the air to flow near the collection surface 34 of the sample substrate 28 such that the charged particles are attracted to the collection surface 34.

According to various aspects of the present invention, the inlet tube 20 defines the first passageway 22 for air to flow from the entry port 12 into the collector housing 14. A first end portion of the inlet tube 20 is coupled to the inlet nozzle 18. A second end portion of the inlet tube 20 is spaced from the sample substrate 28 so as to define a gap between the end of the inlet tube 20 and the sample collection surface 34 of the sample substrate 28. The charging wire 30 is positioned within and towards the second end of the inlet tube 20 such that an electric field is created within the passageway 22 of the inlet tube 20 proximate to the substrate 34. In this regard, a charging point is defined within the passageway 22 of the inlet tube 20 where the electric field charges particulates suspended within the aerosol passing through the collector 10A. As noted above, the sample collection surface 34 of the sample substrate 28 is grounded or held at a charge opposite of the electric field generated within the inlet tube 20. As such, the charging wire 30 defines a point emission electrode and the substrate itself forms a discharge electrode.

When high voltage dc is applied to the charging wire 30, e.g., a dc voltage in the range of 1600 volts to over 11 kilovolts supplied by the high voltage source 32, a corona discharge extends from the point of the charging wire 30 (point emission electrode) to the substrate 34 (discharge electrode). Moreover, precipitation takes place between the two electrodes such that the particulates within the aerosol are collected onto the sample collection surface 34 of the sample substrate 28. The corona discharge extending from charging wire 26 (point emission electrode) towards the collection surface of the substrate 34 has the approximate shape of a cone with the apex at the discharge point and the base at the collection surface. The proximity of the charging wire 30 to the sample substrate 28, the containment of the aerosol to flow through the inlet tube 20 and the draw of the aerosol by the pumping arrangement 40 to force the aerosol to flow near the substrate 34 after charging, collectively and/or individually allow the particulates to be collected into a relatively small area on the collection surface 34 of the sample substrate 28.

Depending upon the specific application, e.g., voltage requirements, electrode material, collection requirements, etc., the positioning of the charging wire 30 to the collection surface of the substrate 28 can be controlled. For example, if the tip of the electrode is positioned too close to the collection surface 34 of the sample substrate 28, it is possible for arcing to occur. If the tip of the electrode is too far from the collection surface 34, then poor collection efficiency/aerosol distribution on the sample substrate may be realized. In an illustrative embodiment, the tip of the electrode may be positioned more than ¼ inch (approximately 0.635 centimeters), but not more than approximately ½ inch (approximately 1.27 centimeters) from the collection surface of the sample substrate. In practice however, the specific circumstances will dictate the appropriate configurations.

According to various aspects of the present invention, the inlet tube 20 may be dimensioned so as to contain the aerosol as it moves a short distance from the charging point to the sample collection surface 34 of the sample substrate 28. As noted in greater detail above, a gap may be present between the end of the inlet tube 20 and the sample substrate 28. However, the inlet tube 20 may be spaced sufficiently close to the substrate 34 so as to force the air flow of the aerosol exiting the inlet tube 20 to get sufficiently close to the substrate 34 to collect particulates thereon, e.g., in a small collection area.

According to various aspects of the present invention, no heat or other feature is utilized to prevent precipitation in the inlet tube itself. Rather, the sample times are kept substantially short. Moreover, the material of the tube itself, e.g., Delrin® acetal resin in the above example, is useful in reducing the precipitation/buildup in the tube. Moreover, the collector 10A according to various aspects of the present invention does not run in a continuous manner. Rather, there may be stops in the collection process, which allows time for the electrode of the charging device 26 to dissipate. Since the field generated by the electrode has time to dissipate, the potential for contamination build up within the collector 10A is minimized.

Thus, the collector 10A, according to various aspects of the present invention, attempts to deposit the material into as small an area as possible by containing the aerosol in the inlet tube 20 and by forcing the aerosol to flow near the sample collection surface 34 of the sample substrate 28 after charging the particles pulled through the inlet tube 20 by the electric field generated by the charging device 26. As noted above, the sample collection surface 34 is held at a neutral or opposite charge relative to the electric field generated by the charging device 26, so the attractive forces of the charged particles to the sample collection surface 34 facilitate collection of the particulates onto the sample substrate 28. By sampling at a low rate, very high efficiencies are possible.

According to various aspects of the present invention, the collector 10A may be constructed to have a small footprint. By way of example, the inlet tube 20 may have an inside diameter of 6 millimeters or less and have a length of approximately 3 inches (approximately 7.62 centimeters) or less. The pumping arrangement 40 may be implemented by a single pump that has dimensions of approximately 1-2 inches (approximately 2.54-5.08 centimeters). As such, the collector 10A may have a footprint of approximately 4 inches by 4 inches (approximately 10.16 centimeters by 10.16 centimeters).

Although the collector 10A may be configured to use small amounts of power, the high voltage power supply 32 should be capable of generating sufficient voltage to cause the charging device 26 to generate an electric field that is sufficient to cause particles carried by the aerosol to collect on the sample substrate 26. As noted above, the high voltage power source 32 may generate a dc voltage in the range of 1600 volts to over 11 kilovolts.

Figure 2:
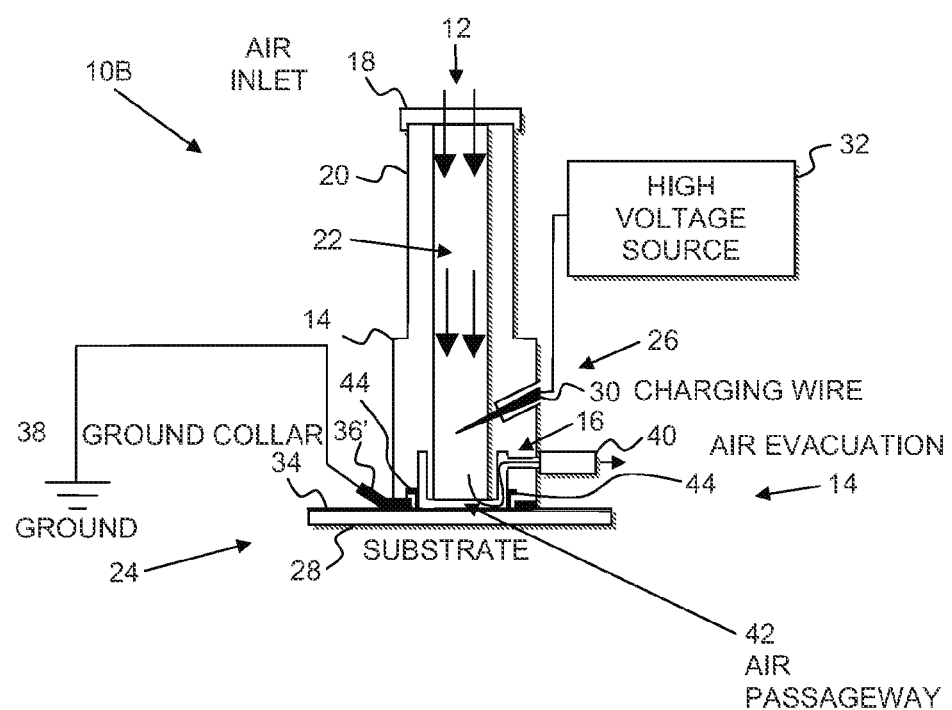
FIG. 2 is a schematic illustration of another small area electrostatic aerosol collector according to various aspects of the present invention.

Referring to FIG. 2, a collector 10B is illustrated according to further aspects of the present invention. The collector 10B is similar in many respects to the collector 10A described with reference to FIG. 1. As such, like structure is illustrated with like reference numerals. In the collector 10B, instead of exhausting the sampled air from the lower portion of the housing 14, the exit port 16 and corresponding pumping arrangement 40 are relocated to the top of the housing 14. This facilitates automated processes such as advancing or otherwise automatically changing the sample substrate 28.

In particular, air is pulled through the inlet tube 20 towards the collection surface of the sample substrate 28. Particulates in the air are charged when they pass the electrode portion of the charging device 26, and are attracted to the oppositely charged (or grounded-neutrally charged) sample collection surface 34 of the sample substrate 28. The remaining air is evacuated through the air passageway 42 via the pumping arrangement 40 to atmosphere along the upper portion of the collector 10B. In this regard, air is not required to flow under/behind the sample substrate 28, such as illustrated in the exemplary implementation of FIG. 1. Rather, air is directed from the collection surface 34 through the air passageway 42 out the side of the collector housing 14.

In this illustrated example, the ground post 36 is configured as a ground collar, and as such, is represented by the numeric 36' to designate its revised configuration. The ground collar 36' is a generally annular ring that surrounds the inlet tube inner diameter and physically contacts the collection surface 34 of the sample substrate 28.

Moreover, as seen in FIG. 2, the collector 10B further includes a collector seal 44, e.g., a gasket that isolates the region of the collection surface 34 of the sample substrate 28 oriented with respect to the end of the inlet tube for receiving particulates so that the collection area is isolated during sample collection. The collector seal 44 is provided to seal the substrate so that previously collected samples are not contaminated. Thus, multiple collection sites are possible on a single sample substrate.

For example, according to various aspects of the present invention, the collector 10B is suitable for use in automated processes where the sample substrate 28 is changed out, either manually or automatically. As another arrangement, the sample substrate 28 may comprise a tape that is automatically advanced, e.g., using a suitable tape and winding, tensioning mechanisms.

Figure 3:
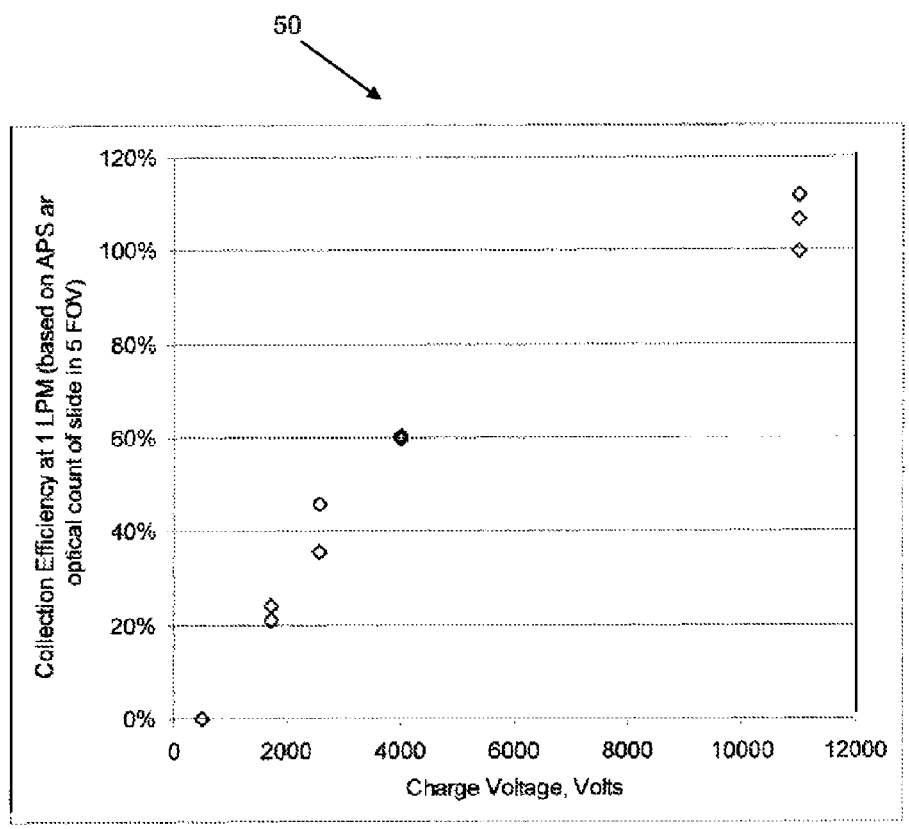
FIG. 3 is a chart illustrating collection efficiency as a function of charge voltage of an exemplary small area electrostatic aerosol collector, such as illustrated in FIG. 1 or FIG. 2, according to various aspects of the present invention.

Referring to FIG. 3, a chart 50 illustrates data points plotting charge voltage (in volts) along the axis of abscissa relative to the collection efficiency of an exemplary implementation of the collector 10 along the axis of ordinate according to various aspects of the present invention. The collection efficiency in the chart of FIG. 3 is a comparison of particulates collected into the collector compared to particulates collected on the sample substrate.

As illustrated in the chart 50, no collection was observed at a charge voltage of 500 volts in the exemplary measurements. However, the collection efficiency was shown to increase with increased voltage between 1600 and 4000 volts. Moreover, near 100% collection efficiency was measured with a charge voltage of 11 kV.

Figure 4:
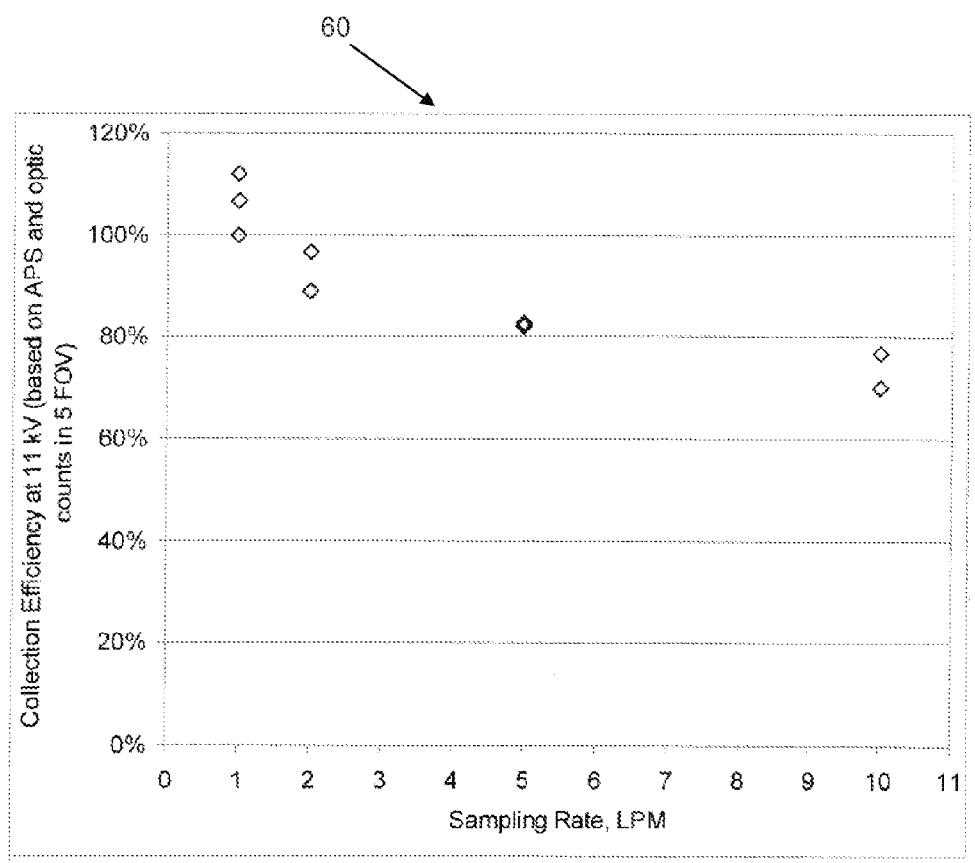
FIG. 4 is a chart illustrating collection efficiency as a function of sampling rate of the small area electrostatic aerosol collector, such as illustrated in FIG. 1 or FIG. 2, according to various aspects of the present invention.

Referring to FIG. 4, a chart 60 illustrates data points plotting sampling rate, in liters per minute (LPM)), along the axis of abscissa relative to the collection efficiency of an exemplary implementation of the collector 10 along the axis of ordinate according to various aspects of the present invention. The collection efficiency in the chart of FIG. 4 was measured at 11 kilovolts based on APS and optic counts in 5 FOV. As illustrated in the chart 60, the collection efficiency (in percent) increases as the sampling rate decreases.

Figure 5:
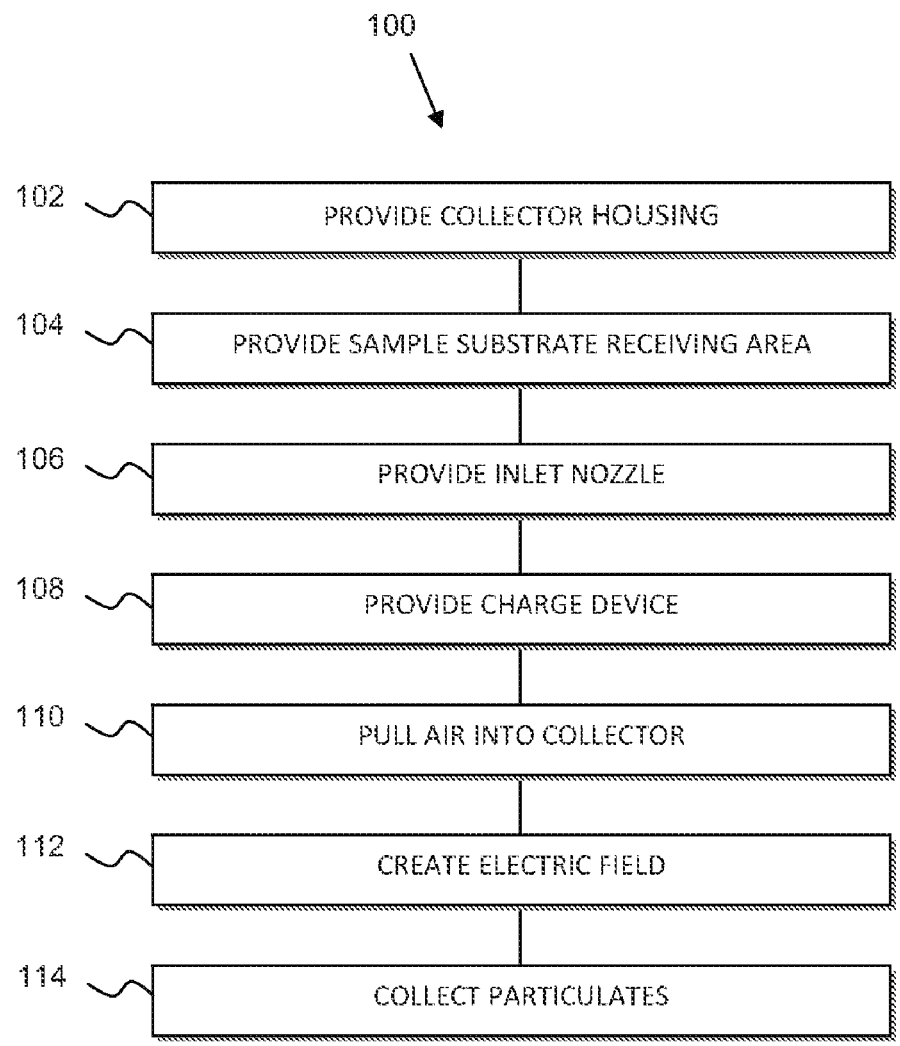
FIG. 5 is a flow chart illustrating a method of particulate collection according to various aspects of the present invention.

Referring to FIG. 5, a method 100 of collecting particulates is illustrated. The method comprises providing a collector housing at 102 and providing a sample substrate receiving area within the collector housing at 104. The method further comprises providing an inlet nozzle at 106, e.g., that extends from the collector housing to provide an inlet for air to flow from outside of the collector housing to the inside of the collector housing and providing a charging device at 108 having an electrode that extends within the passageway.

Still further, the method comprises performing a sampling operation. A sample substrate having a collection surface is positioned in the sample substrate receiving area. The sampling operation is performed by pulling air into the collector housing at 110, e.g., through the inlet nozzle so as to draw the air towards the sample substrate receiving area through a passageway, and evacuating air drawn into the collector housing. For instance, air may be pulled into the collector housing by controlling sampling at a low rate, e.g., on the order of 1-3 liters of air per minute. The sampling operation is further performed by causing the electrode of the charging device to create an electric field at 112 that charges particles in the air flowing past the electrode. For instance, the sampling operation may cause the electrode of the charging device to create an electric field, e.g., by applying a voltage to the electrode at up to or exceeding 11 kilovolts DC, for a short sampling time and then allow the electrode to dissipate sufficient to reduce contamination buildup in the passageway.

The sampling operation is still further performed by holding the collection surface of the sample substrate at one of: a neutral charge and an opposite charge, relative to the electric field created by the charging device and by collecting particulates on the collection surface of the sample substrate at 114 by containing the aerosol in a small area within the passageway and by forcing the air to flow near the collection surface of the sample substrate such that the charged particles are attracted to the collection surface.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention.

Having thus described the invention of the present application in detail and by reference to embodiments thereof, it will be apparent that modifications and variations are possible without departing from the scope of the invention defined in the appended claims.

What is claimed is:

1. A small area electrostatic aerosol collector comprising:
a collector housing;
an inlet nozzle that extends from the collector housing to provide an inlet for air to flow from outside of the collector housing to the inside of the collector housing;
a sample substrate receiving area within the collector housing;
a passageway for air to flow from the inlet nozzle to the sample substrate receiving area, the passageway extending perpendicular from the sample substrate receiving area;

a charging device having an electrode that extends into the passageway at an angle non-parallel to the passageway such that the tip of the electrode is generally centered in the passageway; and a high voltage power source coupled to the charging device;

wherein, a sample substrate having a collection surface is positioned in the sample substrate receiving area and a sample operation is performed such that:

a pumping arrangement pulls air into the collector housing through the inlet nozzle, draws the air towards the sample substrate receiving area through the passageway, and evacuates air drawn into the collector housing;

the high voltage power source causes the electrode of the charging device to create an electric field that charges particles in the air flowing past the electrode;

the collection surface of the sample substrate is held at one of: a neutral charge and an opposite charge, relative to the electric field created by the charging device; and particulates are collected on the collection surface of the sample substrate by containing the aerosol in a small area within the passageway and by forcing the air to flow near the collection surface of the sample substrate such that the charged particles are attracted to the collection surface.

2. The small area electrostatic aerosol collector according to claim 1, wherein the electrode of the charging device comprises at least one charging wire.

3. The small area electrostatic aerosol collector according to claim 1, wherein the electrode of the charging device comprises a tungsten electrode.

4. The small area electrostatic aerosol collector according to claim 1, wherein the electrode terminates in a point.

5. The small area electrostatic aerosol collector according to claim 1, wherein the passageway is defined by an inlet tube coupled to the inlet nozzle, and an end portion of the inlet tube is spaced sufficiently close to the sample substrate positioned within the sample substrate receiving area so as to force the air flow of the air exiting the inlet tube to get sufficiently close to the collection surface of the sample substrate to collect particulates thereon.

6. The small area electrostatic aerosol collector according to claim 5, wherein the inlet tube has an inside diameter of not more than 6 millimeters.

7. The small area electrostatic aerosol collector according to claim 6, wherein the tip of the electrode is positioned between 0.635 centimeters and 1.27 centimeters from the collection surface of the sample substrate.

8. The small area electrostatic aerosol collector according to claim 5, wherein the inlet tube comprises a nonconductive polyacetal material.

9. The small area electrostatic aerosol collector according to claim 5, wherein a main pressure change occurs at a gap between the tube and the sample substrate, and wherein the pumping arrangement pulls between 1-3 liters of air per minute.

10. The small area electrostatic aerosol collector according to claim 1, wherein the sample receiving surface supports a solid substrate that collects particulates as air is drawn by the pump from the inlet nozzle.

11. The small area electrostatic aerosol collector according to claim 1, wherein the high voltage power source generates a voltage in excess of 1600 volts.

12. The small area electrostatic aerosol collector according to claim 1, wherein the high voltage power source generates a voltage up to approximately 11 kilovolts.

13. The small area electrostatic aerosol collector according to claim 1, further comprising an air passageway oriented such that air drawn through the inlet nozzle is evacuated above the collection surface of the sample substrate.

14. The small area electrostatic aerosol collector according to claim 1, wherein:

the passageway is defined by an inlet tube coupled to the inlet nozzle; and the collection surface of the sample substrate is held at a neutral charge relative to the electric field created by the charging device by a ground collar that surrounds the inner diameter of the inlet tube and grounds the collection surface of the collection substrate.

15. The small area electrostatic aerosol collector according to claim 1, wherein:

the passageway is defined by an inlet tube coupled to the inlet nozzle;

further comprising:

a collector seal that isolates a region of the collection surface of the sample substrate oriented with respect to the end of the inlet tube for receiving particulates so that the collection area is isolated during sample collection.

16. The small area electrostatic aerosol collector according to claim 1, wherein the collection substrate comprises an aluminum covered Mylar tape for automated collection of particulates.

17. A method of collecting particulates comprising:

providing a collector housing;

providing a sample substrate receiving area within the collector housing;

providing an inlet nozzle that extends from the collector housing to provide an inlet for air to flow from outside of the collector housing to the inside of the collector housing;

providing a passageway for air to flow from the inlet nozzle to the sample substrate receiving area, the passageway extending perpendicular from the sample substrate receiving area; and providing a charging device having an electrode that extends within the passageway at an angle non-parallel to the passageway;

wherein a sample substrate having a collection surface is positioned in the sample substrate receiving area and a sampling operation is performed by:

pulling air into the collector housing through the inlet nozzle so as to draw the air towards the sample substrate receiving area through the passageway, and evacuating air drawn into the collector housing;

causing the electrode of the charging device to create an electric field that charges particles in the air flowing past the electrode, wherein the charging device creates the electric field for a short sampling time and then allows the electrode to dissipate sufficiently to reduce contamination buildup in the passageway;

holding the collection surface of the sample substrate at one of: a neutral charge and an opposite charge, relative to the electric field created by the charging device; and collecting particulates on the collection surface of the sample substrate by containing the aerosol in a small area within the passageway and by forcing the air to flow near the collection surface of the sample substrate such that the charged particles are attracted to the collection surface.

18. The method according to claim 17, wherein:
causing the electrode of the charging device to generate an electric field comprises causing the electrode of the charging device to generate an electric field with an approximate shape of a cone with an apex at the electrode and a base at the collection surface.

19. The method according to claim 17, wherein pulling air into the collector is controlled by sampling at a low rate on the order of 1-3 liters of air per minute.

20. The method according to claim 17, wherein causing the electrode of the charging device to create an electric field comprises applying a voltage to the electrode at up to 11 kilovolts DC.

* * * * *